United States Patent [19]

Magill et al.

[11] Patent Number: 4,619,260
[45] Date of Patent: Oct. 28, 1986

[54] TISSUE-RETRIEVING MEANS FOR A SURGICAL SNARE INSTRUMENT

[76] Inventors: John W. Magill, 664 N. Michigan Ave., Chicago, Ill. 60611; Carl F. Wurster, 3413 Sunset Ave., Boise, Id. 83703

[21] Appl. No.: 668,098

[22] Filed: Nov. 5, 1984

[51] Int. Cl.[4] ............................................... A61B 1/72
[52] U.S. Cl. ..................................... 128/309; 128/320
[58] Field of Search .................. 128/320, 303 R, 307, 128/309, 329 R, 356

[56] References Cited

U.S. PATENT DOCUMENTS

| 262,489 | 8/1882 | Slater | 128/307 |
|---|---|---|---|
| 534,433 | 2/1895 | Ermold | 128/309 |
| 606,078 | 6/1898 | Pattberg . | |
| 614,760 | 11/1898 | Richter . | |
| 670,067 | 4/1901 | Heiss . | |
| 676,283 | 6/1901 | Stratmann . | |
| 678,333 | 7/1901 | Ermold . | |
| 678,334 | 7/1901 | Ermold . | |
| 798,839 | 9/1905 | Stowe | 128/320 |
| 1,453,934 | 5/1923 | Lo Giudice . | |
| 1,731,069 | 10/1929 | Herman . | |
| 2,115,298 | 4/1938 | Brown | 128/320 |
| 2,230,431 | 2/1941 | Moore | 128/320 |

OTHER PUBLICATIONS

"The Surgical Armamentarium for Oto-R-hino-Laryngology", V. Mueller Div. of American Hospital Supply Corp., 1974, Title page and pp. 20, 104, 176, 177, and 178.

Primary Examiner—Gene Mancene
Assistant Examiner—John G. Weiss
Attorney, Agent, or Firm—Gerlash & O'Brien

[57] ABSTRACT

Tissue-retrieving means for a surgical instrument having a snare loop projecting outwardly from a distal end thereof for encircling projecting body tissue, and means for contracting the loop, thereby to sever the encircled tissue, which retrieving means includes tissue engaging means, manipulating means connected to the engaging means, means for mounting the manipulating means on the instrument for manipulating the engaging means to engage tissue encircled by the loop, and means for effecting manual adjustment of the position of the engaging means relative to the loop, rotationally about a longitudinally-extending axis, for engagement of the engaging means with a selected portion of encircled tissue extending from either side of the loop. In a preferred embodiment, the tissue-engaging means comprises means for impaling encircled tissue thereon, including a barb movable between a contracted position assumed during insertion into encircled tissue to engage the tissue, and an expanded position assumed upon removal of the tissue on the engaging means.

15 Claims, 9 Drawing Figures

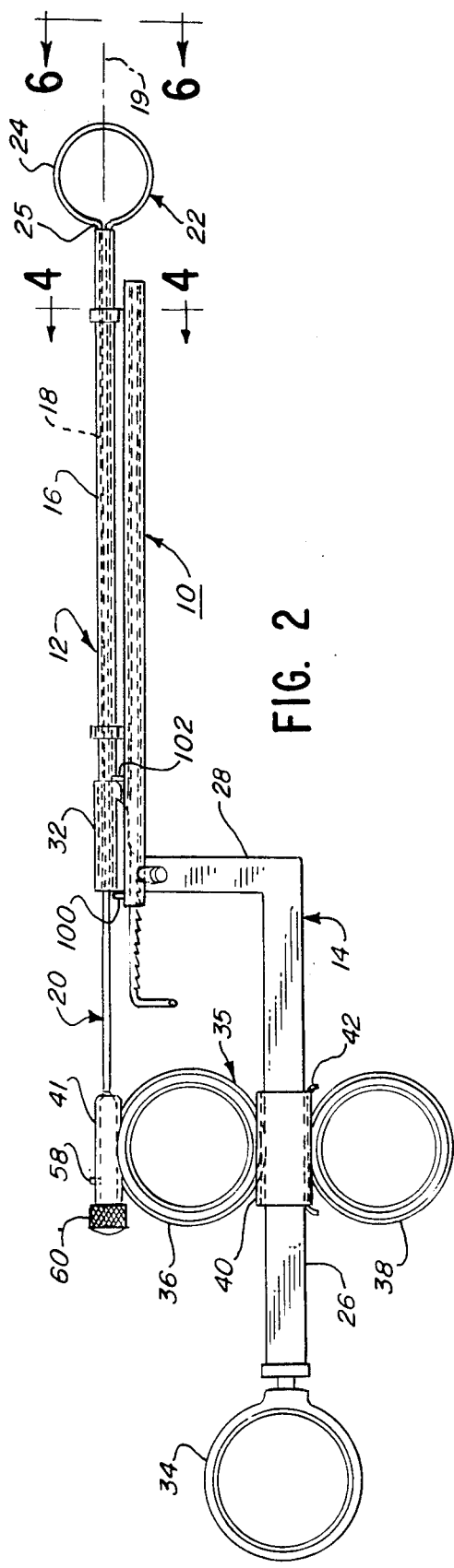
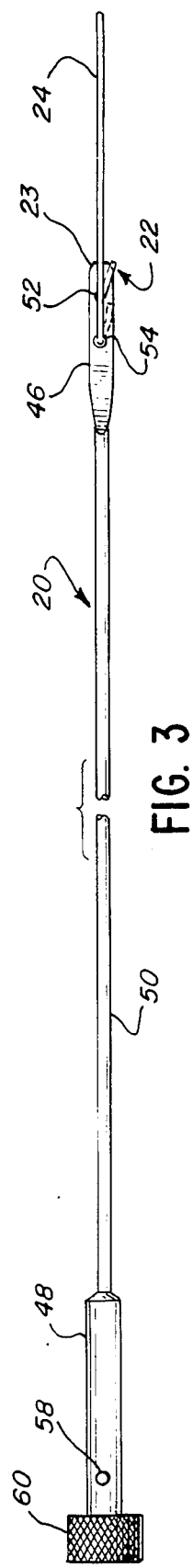
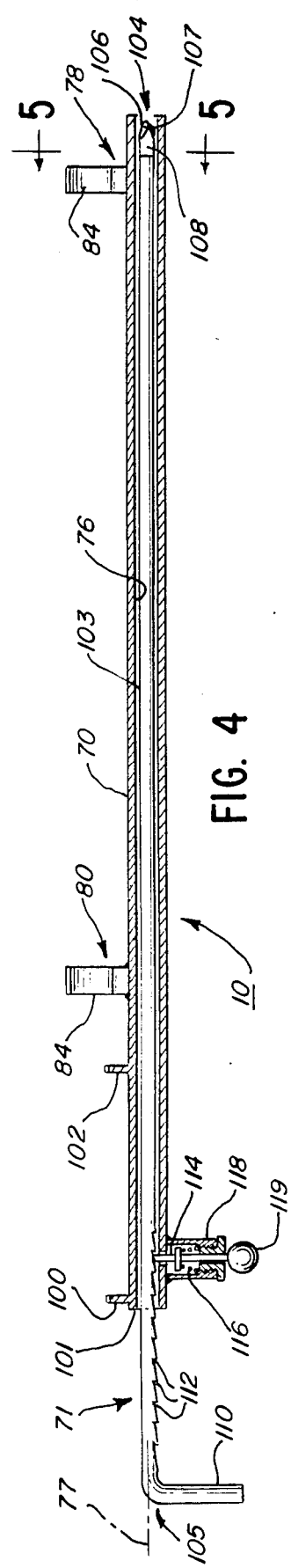
FIG. 2
FIG. 3
FIG. 4

TISSUE-RETRIEVING MEANS FOR A SURGICAL SNARE INSTRUMENT

BACKGROUND OF THE INVENTION

This invention relates to tissue-retrieving means for a surgical open-snare instrument, and, more particularly, to such means and instrument suitable for removing projecting body tissue.

Snare instruments are employed for removing projecting normal and abnormal body tissue, in particular, tonsils and nasal polyps. Such instruments utilize a wire snare, which is lopped around the tissue to be removed, and then is contracted to sever the tissue from the body as the loop is reduced in size.

A surgical snare instrument typically comprises a barrel, and a resilient snare loop-forming wire carried by the barrel. The instrument is handheld and has mechanism enabling a surgeon to extend the wire beyond the distal end of the barrel, where it is expanded to form a loop for encircling projecting body tissue. The wire then may be retracted into the barrel, thereby contracting the loop, which cuts through the encircled body tissue as it contracts.

Two types of surgical snare instruments have been used: those having a "covered" snare, and those having an "open" snare. Covered-snare instruments have an annular structure at the distal end of the barrel, which receives and shapes the snare loop. Both the loop and the receiving structure encircle the body tissue, and the tissue is severed by contracting the loop. Open-snare instruments have no loop-receiving structure, but the snare loop is freely formed and contracted at the distal end of the barrel. An open-snare instrument is preferred for use in removing nasal polyps, to minimize bulk and obstruction of the field of view, and permit the loop to be adjusted freely, according to the situation. The present invention is concerned with open-snare instruments.

When nasal polyp or tonsil tissue is severed from the body by means of a snare instrument, it is necessary to retrieve or recover the severed tissue, avoiding inhalation or swallowing of the tissue in the process. Most frequently, polyps and tonsils are removed by an aspiration or suction device, operated by an assistant to the surgeon using the snare instrument. Previously, various tonsilotomes have been proposed that incorporate a harpoon-like tissue-retriever, on which the tissue is impaled, for removal after being severed from the body. However, we are not aware that such prior tonsilotomes are being sold now, or that the same or similar instruments are being sold for other purposes, particularly for use as nasal snares, or that any open-snare instrument has been provided with any kind of tissue-retrieving means.

Nasal polypectomies pose unique problems. Usually, they are carried out with the patient in a reclining position, and, often, under only local anesthesia. The windpipe of a patient under local anesthesia is not shielded by the endotracheal tube commonly employed when general anesthesia is used. Hence, when a polypectomy is performed under local anesthesia, precautions must be taken to prevent the severed polyp from falling through the nasal passages of the patient into the nasopharynx, where it may be inhaled and block the patient's airway. If an inhaled polyp is not coughed up by the patient, major medical procedures may be necessary to remove it.

In polypectomies, the snare loop typically is positioned to sever the portion of the polyp—the "stalk"—connecting the body of the polyp to the wall of the nostril. To minimize the risk of having the severed polyp fall back into the nasal passage, and to make it easier for an assistant to aspirate it, the surgeon often will not cleanly sever the polyp by completely contracting the loop about the encircled polyp stalk. Instead, the surgeon will partially contract the loop, thereby partially cutting through the stalk, then will complete the removal of the polyp by avulsion: by pulling the wire through the remainder of the stalk, thereby tearing away the polyp while tending to pull it forward out of the nostril. However, avulsion of a polyp tends to produce greater tissue damage, bleeding, and patient discomfort, then does clean severing thereof.

SUMMARY OF THE INVENTION

Important objects of the present invention include the provision of tissue-retrieving means for a surgical open-snare instrument, which means will insure that severed tissue is removed from within the body, and will reduce the risk of inhaling or swallowing the tissue where such danger exists, which may be used in close quarters, which enables the surgeon to both sever the tissue and also, if desired, simultaneously to retrieve the severed tissue without assistance, and which is manipulatable for engagement with a selected portion of the tissue and at various locations relative to the snare loop.

The invention provides tissue-retrieving means for a surgical open-snare instrument having a snare loop projecting longitudinally outwardly from a distal end thereof for encircling projecting body tissue, and means for contracting the loop, thereby to sever the encircled tissue from the remainder of the body. The retrieving means includes tissue-engaging means, manipulating means connected to the engaging means, means for mounting the manipulating means on the instrument for manipulation of the engaging means to engage tissue encircled by the loop, for removal of the tissue on the engaging means following severance of the tissue, and means for effecting manual adjustment of the position of the engaging means relative to the loop, rotationally about a longitudinally extending axis, for engagement of the engaging means with a selected portion of encircled tissue extending from either side of the loop.

In a preferred embodiment of the invention, the tissue-engaging means comprises means for impaling encircled tissue thereon, which includes a barb movable between a contracted position assumed during insertion into encircled tissue to engage the same, and an expanded position assumed upon removal of the tissue on the engaging means.

In another preferred embodiment of the invention, a finger-engageable handle is provided on the tissue-retrieving means, for facilitating the operation of the snare loop and of the tissue-engaging means with the same hand.

Inasmuch as the tissue-retrieving means of the invention provides means for engagement of tissue prior to its severance, the tissue need not be avulsed in a effort to prevent undesired displacement of tissue from the site of the surgical procedure. Instead, the tissue may be cleanly severed, with resulting lessened injury and discomfort to the patient.

BRIEF DESCRIPTION OF THE DRAWINGS

The attached drawings illustrate preferred embodiments of the invention, without limitation thereto. In the drawings, like elements are identified by like reference symbols in each of the views, and:

FIG. 2 is a side elevational view of the assembly, enlarged with respect to FIG. 1.

FIG. 3 is a further enlarged, broken plan view of a snare-operating bar of the instrument, with a snare mounted thereon.

FIG. 4 is an enlarged longitudinal sectional view, partly in elevation, of the tissue-retrieving means, taken substantially on line 4—4 of FIG. 5.

FIG. 5 is an enlarged broken transverse sectional view of the tissue-retrieving means, taken substantially on line 5—5 of FIG. 4.

FIG. 6 is an enlarged and elevational view of the assembly, taken substantially on line 6—6 of FIG. 2, illustrating alternative positions of the tissue-retrieving means in phantom lines.

FIG. 7 is a greatly enlarged fragmentary perspective view of a retriever in the tissue-retrieving means, illustrating tissue-engaging means at a distal end thereof.

FIG. 8 is an enlarged fragmentary longitudinal sectional and elevational view of an assembly similar to the preceding views, shown in use, having, however, modified structure for mounting the tissue-retrieving means.

FIG. 9 is a fragmentary elevational view of an assembly similar to that of the preceding views, showing the structure adjacent to a distal end thereof, and illustrating a modified form of retriever.

DESCRIPTION OF THE PREFERRED EMBODIMENTS

Figure 1:
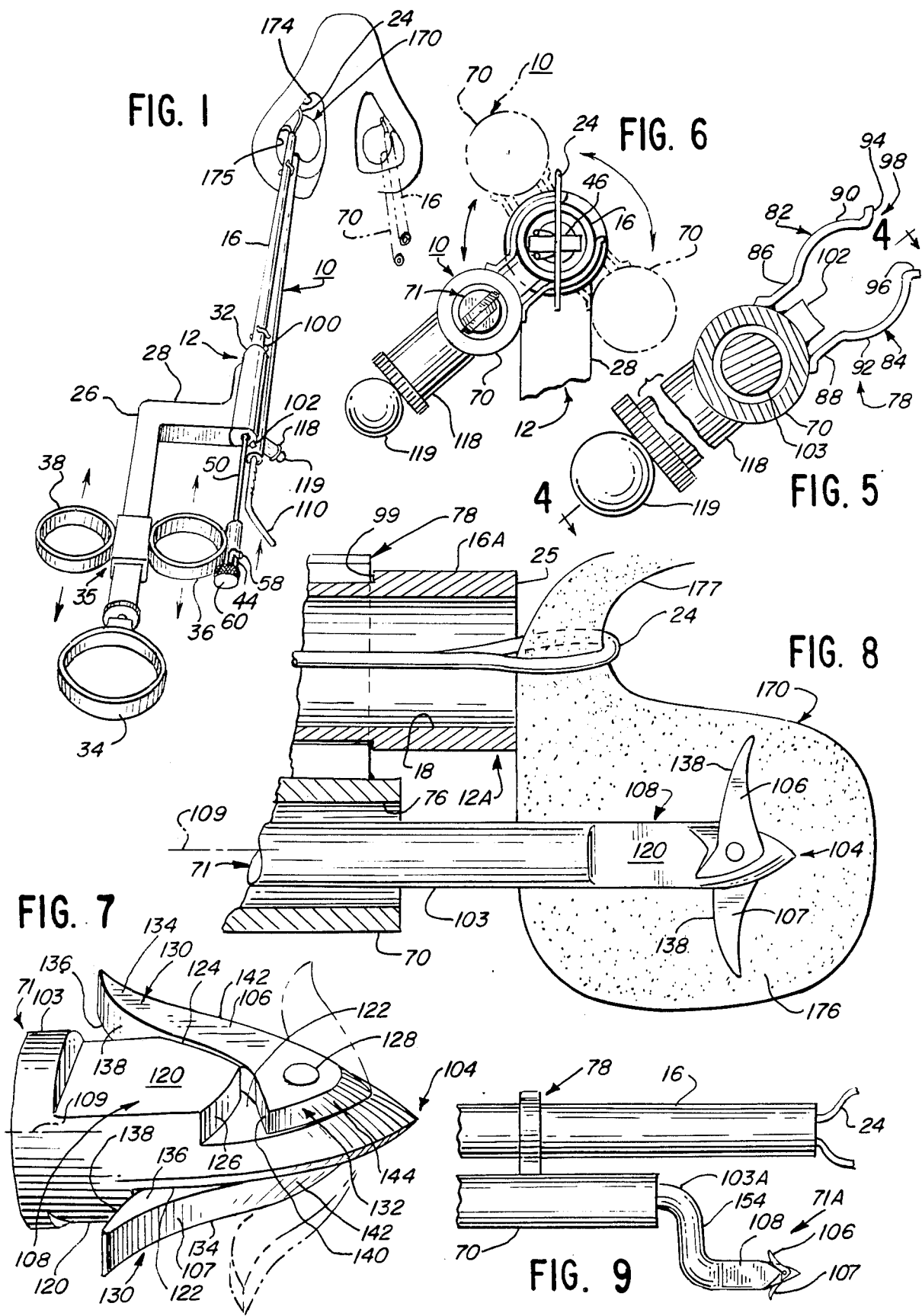
FIG. 1 is a perspective view of an assembly of tissue-retrieving means mounted on an open-snare surgical instrument, in accordance with the invention. The assembly is shown, schematically, in use removing a nasal polyp.

Referring especially to FIGS. 1 to 3 of the drawings, tissue-retrieving means 10 is mounted on a surgical open-snare instrument 12, in accordance with the invention.

The instrument 12 is a conventional nasal snare instrument. It includes a frame member 14, and, connected thereto, a longitudinally extending tubular barrel 16 having a bore 18 with a longitudinal axis 19. A snare-operating bar or rod 20 is carried by the barrel 16, for longitudinal reciprocatory movement in the bore 18. A wire snare 22 is connected to the bar 20 adjacent to a distal end 23 of the bar, for forming a snare loop 24 which projects longitudinally outwardly or forwardly from a distal or front end 25 of the barrel 16.

The frame member 14 is generally L-shaped, having a longitudinally-extending shank 26, a riser 28 at a distal end of the shank, and a collar 32 on a free end of the riser. The shank and the riser are integral with each other and are rectangular in cross section. The collar 32 extends longitudinally of the instrument 12, and it is fixed, as by welding, brazing, soldering, or the like, to the riser 28. The proximal or rear end of the barrel 16 is received in the collar 32 and similarly fixed thereto.

A thumb grip 34 extends rearwardly from the proximal end of the shank 26 and is mounted for pivotal movement thereon. A finger-grip unit 35 is longitudinally slidably mounted on the shank 26. The unit 35 includes two finger grips 36 and 38, fixedly mounted, as by welding or brazing, to opposite sides of a rectangularly tubular carriage 40. The carriage 40 is slidably mounted on the shank 26, which extends therethrough. A leaf spring 42 is interposed between the shank 26 and the carriage 40, to minimize play and restrict sliding movement of the unit 35.

A cylindrically tubular sleeve 41 is fixedly mounted on the outer side of one finger grip 36 of the unit 35, with its longitudinal axis substantially coaxial with that of the collar 32. An L-shaped bayonet slot 44 (FIG. 1) is provided in the sleeve 41 at a proximal end thereof.

Referring to FIG. 3, the snare-operating bar 20 includes a flattened distal end portion 46, and a cylindrical proximal end portion 48. A cylindrical shaft 50, of smaller diameter than the proximal end portion 48, extends longitudinally therefrom to the distal end portion 46. The shaft 50 and the distal end portion 46 are dimensioned for reception in the bore 18 of the barrel 16, for longitudinal reciprocatory movement therein.

The distal end portion 46 of the snare-operating bar 20 is provided with holes 52 and 54 which extend transversely therethrough. The snare 22, preferably composed of stainless steel surgical wire, is removably attached to the bar 20 by extending the opposite ends of the wire through respective holes 52 and 54, and bending the ends over the distal end portion 46. The proximal end portion 48 of the bar 20 is provided with a locking pin 58 projecting radially from its side surface and with an enlarged knurled knob 60 mounted on its rear end.

The distal end portion 46 and the shaft 50 of the snareoperating bar 20 are inserted through the sleeve 41 and into the collar 32 and the barrel 16, and the proximal end portion 48 is removably received in the bore of the sleeve 41, as illustrated in FIG. 2. At the same time, the locking pin 58 is received in the bayonet slot 44, for locking the snare-operating bar 20 to the sleeve 41, and thereby to the finger grip unit 35. Reciprocatory longitudinal movement of the finger grip unit 35 on the shank 26 then effects corresponding movement of the bar 20 in the barrel 16.

When the finger-grip unit 35 is in its forwardmost position on the shank 26, the distal end portion 46 of the bar 20 projects from the distal end 25 of the barrel 16, sufficiently to render the holes 52 and 54 accessible for attachment of a snare 22 to the bar 20. The snare is attached so that the round loop 24 may be formed, sufficiently large and with an opening wide enough to enable the loop to be drawn over a polyp, or other projecting tissue, from the free end thereof, and encircle the same. After the snare 22 is attached, the unit 35 may be moved rearwardly on the shank 26, to cause the loop to be contracted by engagement with the adjacent edge of the barrel 16 and from partly to fully drawn into the bore 18 of the barrel. Thereafter, when the finger-grip unit 35 is moved forwardly, the snare 22 is extended longitudinally outwardly from the distal end 25 of the barrel 16. The loop 24 is formed and shaped generally as shown in FIG. 2 with a suitable instrument or tool, and/or with the fingers. In general, the snare loop 24 lies in a plane substantially parallel to or containing the bore axis 19. Alternatively, the loop 24 may be bent out of such plane. The plane of the loop 24 may bear various relationships to the fixed plane of the frame member 14.

Referring to FIGS. 1, 2, 4, and 5, the tissue-retrieving means 10 includes an assembly of an elongate tubular carrier 70, and a retriever 71 carried thereby. The carrier 70 has a cylindrical bore 76 having a longitudinal axis 77. Two resilient split-ring clamps 78 and 80 are fixed to and extend laterally outwardly from the outer surface of the carrier 70, in longitudinally spaced apart relation. Each clamp includes two leaf spring arms 82 and 84 (FIG. 5) or the like, each having an inner shank portion 86 or 88, an intermediate convex barrel-receiving portion 90 or 92, and an outer lip portion 94 or 96. The shank portions 86 and 88 of the clamps are fixedly secured to the carrier in spaced apart, opposed relation, by suitable means, such as welding or brazing. The lip portions define between them a mouth 98, which provides restricted entry to the receiving portions 90 and 92.

The carrier 70 is provided with two longitudinally spaced apart lugs 100 and 102, which extend laterally outwardly from the outer surface of the carrier, adjacent to a proximal end 101 thereof. The lugs are fixed to the carrier by suitable means, such as welding or brazing.

The carrier 70 is removably mounted on the instrument 12 by engaging the clamps 78 and 80 with the barrle 16. Thus, the barrel 16 is inserted between the lips 94 and 96 of each clamp, and the lips spread resiliently, to allow the barrel to seat rotatably on the receiving portions 90 and 92. The carrier is laterally spaced from the barrel by the shank portions 86 and 88.

The respective distal and proximal ends of the carrier and barrel are disposed adjacent to one another. In the illustrative embodiment, the longitudinal axes 19 and 77 of the bores 18 and 76 of the barrel 16 and the carrier 70, respectively, are substantially parallel. As illustrated in FIGS. 1 and 2, the lugs 100 and 102 embrace the collar 32, so that movement of the carrier relative to the barrel is prevented by abutment of the lugs 100 and 102 with the opposite end surfaces of the collar.

Alternatively, the lugs 100 and 102 may be omitted, and, as illustrated in FIG. 8, a modified barrel 16A of an instrument 12A may be provided with an annular groove 99 therearound, in spaced apart adjacent relation to the distal end 25 of the barrel. A like groove, not shown, may be provided in the barrel 16A in spaced apart adjacent relation to the collar 32. Such grooves 99 are spaced apart from the same distance as the clamps 78 and 80, whereby the clamps may be received in respective grooves, for preventing movement of the carrier 70 relative to the barrel 16A.

The curvatures of the receiving portions 90 and 92 of the clamps conform substantially to the curvature of the barrel 16, or of the groove 99 in the modified barrel 16A, for snugly clamping the barrel therebetween. Preferably, the frictional force exerted on the barrel 16 or 16A by the arms 82 and 84 is such that the carrier 70 can be rotated manually around the barrel, about the longitudinal axis 19 of the barrel and its bore 18, without undue effort, and when once moved, will not readily slip out of position. It will be apparent to those skilled in the art that more positive means can be used to ensure that the carrier 70 remains fixed in a selected angular position relative to the barrel. For example, a screw opening (not shown) may be provided in a clamp spring 82 or 84, and a thumbscrew (also not shown) may be extended therethrough, for bearing on the barrel.

Referring particularly to FIG. 4, the retriever 71 includes an elongate manipulating rod 103 having a pointed distal end 104 and a bent proximal end 105, and a pair of barbs 106 and 107 pivotally mounted on a mounting portion 108 of the manipulating rod adjacent to its distal end 104. Rod stock is bent substantially at a right angle to form a finger-engageable receiver handle 110 at the proximal end 105 of the rod 103 and integral therewith. The rod 103 is received in the bore 76 of the carrier 70, with the bore axis 77 parallel to or coincident with the longitudinal axis 109 (FIGS. 7 and 8) of the rod. The rod 103 is longitudinally reciprocable in the bore 76, for like movement of the retriever 71. The handle 110 is disposed in the vicinity of or proximate to the finger grip unit 35, for manual control of the movement of both the snare loop 24 and the rod 103 by the same hand.

Ratchet teeth or serrations 112 are provided in the rod 103 adjacent to the proximal end 105 thereof. The teeth 112 cooperate with a latching pawl 114 to interengage the rod 103 and the carrier 70 in such a manner as to permit longitudinal movement of the rod towards its distal end 104. The pawl 114 and a spring 116 resiliently biasing the pawl into latching contact with the teeth are contained in a casing 118 fixed to the carrier 70 and extending laterally therefrom. The pawl 114 is unlatched from the teeth by moving it laterally away from the carrier against the restoring force of the spring, pulling on a knob 119 on the outer end of the pawl for that purpose.

Referring to FIGS. 7 and 8, the barb-mounting portion 108 constitutes a shaped or cut-out portion of the manipulating rod 103, formed by suitable means, such as grinding or stamping. The mounting portion 108 in the illustrative embodiment includes like parallel substantially planar outer surfaces 120 on opposite sides of the rod axis 109. Like parallel substantially planar inner surfaces 122 are provided on the mounting portion 108, on opposite sides of the rod axis 109, and they are longitudinally disposed between the outer surfaces 120 and the distal end 104 of the rod. The outer surfaces 120 are equidistantly spaced from the rod axis 109, and the inner surfaces 122 are equidistantly spaced from the axis 109, the latter at lesser distances from the axis, whereby transverse stop surfaces 124 and 126 are formed at the leading edges of the outer surfaces 120, and intersect in angular relation to each other. As best been in FIG. 7, the mounting portion 108 in the illustrative embodiment is bevelled and brought to a point at the distal end 104, to facilitate penetration of tissue by the rod 103 at such end.

The barbs 106 and 107 are alike, and each is mounted for pivotal movement about a transverse axis, on a planar inner surface 122, by means of a pivot pin 128 that extends transversely through the rod 103, in spaced apart relation to the distal end 104 and intersecting the inner surfaces 122. Referring to one barb 106 as representative of both of the illustrative barbs, the structure resembles a bell crank lever having respective long and short arms 130 and 132. The arms have, in common, parallel substantially planar outer and inner surfaces 134 and 136, respectively. The arms intersect angularly, and the pivot pin 128 extends transversely through the barb, intersecting its surfaces 134 and 136 perpendicularly thereto, at the apex formed by the arms and adjacent to the distal end 104 of the rod. With the barb 106 thus mounted on the mounting portion 108, its inner surface 136 is movable rotationally on an inner surface 122 of the mounting portion, and its outer surface 134 is substantially coplanar with the outer surface 120 of the mounting portion.

The long arm 130 of each barb 106 and 107 in the illustrative preferred embodiment extends laterally outwardly from the rod 103, and is movable rotatably from a contracted position of the barb, illustrated in full lines in FIG. 7, to an expanded position, illustrated in broken lines, by clockwise rotation as viewed in FIG. 7 for the upper barb 106. The long arm 130 has a preferably curved or arcuate trailing surface 138 which abuts on an adjacent stop surface 124 in the contracted position. The short arm 132 has a trailing surface 140 that is spaced from the remaining stop surface 126 when the long arm 130 is in such abutting position, and abuts on the remaining stop surface 126 when the long arm is in its expanded position.

In this manner, the abutment of the trailing surfaces 138 and 140 on the respective stop surfaces 124 and 126 determines the contracted and expanded positions of the barbs 106 and 107, with the barbs extending from the axis of the pivot pin 128 towards the proximal end 105 of the rod 103 at respective lesser and greater angles to the longitudinal axis 109 of the rod, referring to the angles made with such axis by the long arm 130 serving to engage tissue. In the illustrative preferred embodiment, the barbs 106 and 107 are contracted to facilitate insertion into tissue, and they expand upon tissue retrieval. In their contracted positions, the barbs are retractable with the mounting portion 108 into the bore 76 of the carrier 70. As an example of the width dimensions, the width of the retriever 71 across the barbs 106 and 107, measured between the trailing ends or tips of the long arms 130, may be about 3/32 inch when the barbs are contracted, as in FIG. 7, and about 3/16 inch when expanded, as in FIG. 8. The diameter of the bore 76 in the preferred embodiment is greater than the width across the contracted barbs, to accomodate the barbs therewithin and also permit removal of the retriever 71 from the carrier 70.

The outer ends of the long arms 130 preferably project beyond the sides of the rod 103 in the contracted positions of the barbs 106 and 107, as illustrated in FIG. 7, to facilitate engagement with the tissue and expansion of the barbs upon relative movement of the rod in the direction of its proximal end 105. The long and short arms 130 and 132 of each barb have respective leading surfaces 142 and 144 that intersect angularly at the apex or tip of the barb, and may be bevelled to correspond to the adjacent surfaces of the mounting portion 108, as illustrated in FIG. 7, to facilitate tissue penetration at the pointed distal end 104 of the rod 103. The preferred material of construction of the retriever 71, including the barbs 106 and 107, is surgical stainless steel.

The assembly of FIG. 9 is provided with a modified retriever 71A, and otherwise is constructed in the same manner as the assembly illustrated in FIGS. 1-7. The modified retriever 71A includes a modified manipulating rod 103A having the same barb-mounting portion 108 and barbs 106 and 107 thereon as illustrated in FIG. 7, at the distal end of the rod. The mounting portion 108 is laterally offset from the main body of the rod 103A, by means of a laterally projecting rod segment 154 interposed between the main body of the rod and the mounting portion, and joined thereto by right angle bends. To enable removal of the retriever 71A from the carrier 70, the handle 110 shown in preceding views may be replaced by a similar but detachably connected handle, not illustrated. Alternatively, the rod segment 154 may be detachably connected to the main body of the rod 103A. In either case, the detachable connection may be made by screw thread or other suitable connecting means.

Use of the assembly of tissue-retrieving means 10 and the instrument 12 or 12A is illustrated in FIGS. 1 and 8. The assembly is shown in use for removing a nasal polyp 170 growing in the right nostril 174 (left-hand side of the view) of a reclining patient and projecting from a lateral wall 175 of the nostril. Nasal polyps often resemble a grapelike body growing on a stalk or stem, and can vary in size considerably.

Initially, the snare 22 may be more or less retracted into the bore 18 of the barrel 16. The distal end 104 of the retriever 71 advantageously may be retracted into the bore 76 of the carrier 70, to obviate catching or snagging a barb 106 or 107 on tissue unintentionally. The surgeon, by use of the finger-grip unit 35, extends the snare-operating bar 20 forwardly in the barrel 16, to project the snare 22 beyond the distal end of the barrel. The snare 22 is expanded and formed into the generally planar snare loop 24. The size or diameter of the loop 24 is adjusted to be large enough to pass around the body 176 (FIG. 8) of the polyp.

After the loop 24 is formed, the surgeon passes it over the body 176 of the polyp to encircle the stalk 177 thereof, and then retracts the snare-operating bar 20 in the barrel 16, to snug the loop 24 about the stalk, as illustrated in FIG. 8. The tissue-retrieving means 10 may be rotated around the barrel 16, if necessary, to bring the retriever 71 into an optimum position for engaging the body 176 of the polyp 170, as illustrated in phantom lines in FIG. 6. The retriever 71 preferably is directed towards a generally central portion of the body 176 of the polyp. The optimum position of the retriever 71 relative to the loop 24 depends on factors such as the size of the polyp, its location on the lateral wall of the nostril, the extent to which the body of the polyp droops or sags under the influence of gravity, and the movement of the polyp caused by the respiration of the patient. The range of adjustment of the tissue-retrieving means 10 on the instrument 12 or 12A and the ability to make incremental adjustments accommodate variations caused by such factors.

The retriever 71 next is advanced for penetration of the polyp, by moving the manipulating rod 103 in the direction of its distal end 104. Penetration is facilitated by the pointed configuration of the distal end 104 and by the compact contour of the barbs 106 and 107 in the contracted position they assume when urged rearwardly by the reaction force of the penetrated tissue on the leading surfaces 142 of the long arms 130 of the barbs. The retriever 71 then may be retracted slightly, to cause the barbs 106 and 107 to expand in the polyp, as shown in FIG. 8.

The handle 110 of the manipulating rod 103 being located near to the finger grip unit 35, the surgeon is enabled to use the same hand to manipulate both the snare loop 24 and the retriever 71. One-handed use of the assembly also is facilitated by the ratchet structure of teeth 112 and pawl 114, which functions automatically to retain the rod 103 in its longitudinally forward tissue-penetrating position. The other hand of the surgeon then is available for tasks which may be more efficiently performed by the surgeon then by an assistant, such as positioning and manipulating an aspirator for removing blood.

After the polyp 170 has been impaled, the snare 22 is retracted completely into the barrel 16, thereby substantially completely closing the loop 24 and cutting through the encircled stalk 177, to sever it from the remainder of the body. If the barbs 106 and 107 have not already been set in their expanded positions, the reaction forces exerted by the tissue of the polyp on the trailing surfaces 138 of the long arms 130 cause the barbs to pivot into their expanded positions, illustrated in FIG. 8. In such positions, the barbs are widespread, and substantially the entire trailing surfaces 138 of the barbs are in engagement with polyp tissue, for removal of the polyp on the retriever 71 without separation of the two.

The mounting of the tissue-retrieving means 10 on the barrel 16 enables such means to be disposed on either of the opposite sides of the snare instrument 12, as illustrated in full and phantom lines in FIGS. 1 and 6, for engagement of the retriever 71 with a snare-encircled polyp 170 or other tissue extending from either side of the snare loop 24. For this purpose, the carrier 70 may be rotated about the barrel 16 to an extent limited in the illustrative embodiment only abutment of the carrier on the opposite sides of the frame riser 28, i.e., preferably to the extent of at least 180 degrees of rotation. The surgeon, therefore, is enabled to remove a polyp 170 from either nostril, with but little change in technique from one to the other, and following the same general procedure as when using the snare instrument 12 without the retrieving means 10.

The retriever 71, having the barbs 106 and 107, which are movable to expanded positions, is particularly advantageous for use in engaging and removing tissue which has relatively little strength or firmness. Such tissue typically is found in nasal polyps, which resemble mucus-filled bags. On the other hand, relatively narrow tissue-engaging means with a relatively small area bearing on such tissue may have a tendency to tear through and out of such tissue, to leave it behind. The invention also may be employed for removing other projecting body tissue, including tonsils, uterine growths, and intestinal growths, and is especially advantageous for use in confined spaces, owing to its compact, adjustable nature. The modified retriever 71A of FIG. 9 may be preferred for use in instances where the tissue portion to be penetrated is farther removed from the snare loop 24.

The tissue-retrieving means 10 is constructed for attachment to the conventional open-snare instrument 12 at any time, so that it may be employed as part of a factory assembly with a new instrument or as a retrofit with an instrument in use. The retrieving means may be detached from the instrument, if desired. Alternatively, the carrier 70 or a modification thereof may be mounted on an instrument in a permanent fashion, if desired, by means not illustrated.

While preferred embodiments of the invention have been illustrated and described, and reference has been made to certain changes and modifications which may be made therein, it will be apparent to those skilled in the art that further changes and modifications may be made therein within the spirit and scope of the invention. It is intended that all such changes and modifications be included within the scope of the appended claims.

We claim:

1. Tissue-retrieving means for a surgical open-snare instrument having a snare loop projecting longitudinally outwardly from a distal end thereof for encircling projecting body tissue, and means for contracting the loop, thereby to sever the encircled tissue from the remainder of the body, said retrieving means comprising:
    tissue-engaging means,
    manipulating means connected to said engaging means,
    means for mounting said manipulating means on said instrument for manipulation of said engaging means to engage tissue encircled by said loop, for removal of the tissue on the engaging means following severance of the tissue, and
    means for manually effecting rotational adjustment of the position of said engaging means relative to said loop about an axis extending longitudinally of the open-snare instrument for engagement of said engaging means with a selected portion of encircled tissue extending from either side of said loop.

2. Tissue-retrieving means as defined in claim 1 wherein said tissue-engaging means comprises means for impaling encircled tissue thereon.

3. Tissue-retrieving means as defined in claim 2 wherein said impaling means comprises a barb movable between a contracted position assumed during insertion into encircled tissue to engage the same, and an expanded position assumed upon said removal of the tissue on the engaging means.

4. Tissue-retrieving means for a surgical open-snare instrument having a longitudinally extending barrel, a snare loop projecting longitudinally outwardly from a distal end of the barrel for encircling projecting body tissue, and means carried by the barrel for contracting the loop, thereby to sever the encircled tissue from the remainder of the body, said retrieving means comprising:
    tissue-impaling means,
    manipulating means connected to said impaling means,
    means for mounting said manipulating means on said barrel for moving said impaling means longitudinally to impale tissue encircled by said loop, for removal of the tissue on the impaling means following severance of the tissue, and
    means for manually effecting rotational adjustment of the position of said mounting means about the longitudinal axis of the barrel thereby to adjust the position of said impaling means relative to said loop for engagement of said impaling means with a selected portion of encircled tissue extending from either side of said loop.

5. Tissue-retrieving means as defined in claim 4 further including means for interengaging said manipulating means and said mounting means, to releasably maintain the impaling means in a tissue-engaging longitudinal disposition.

6. Tissue-retrieving means as defined in claim 4 wherein said tissue-impaling means comprises a barb, and said manipulating means extends along a longitudinal axis thereof from a distal end to a proximal end thereof, and further including means mounting said barb on said manipulating means for pivotal movement about a transverse axis between contracted and expanded positions of the barb, wherein the barb extends from the transverse axis in the direction of said proximal end at respective lesser and greater angles to said longitudinal axis of the manipulating means, and means limiting said pivotal movement to movement between said positions.

7. Tissue-retrieving means as defined in claim 6 wherein said manipulating means comprises a rod having distal and proximal ends, said barb is mounted adjacent to the distal end of the rod.

8. Tissue-retrieving means as defined in claim 7 further including means for interengaging said rod and said mounting means, to releasably maintain said impaling means in a tissue-impaling longitudinal disposition.

9. In combination with a surgical open-snare instrument having a snare loop projecting longitudinally outwardly from a distal end thereof for encircling projecting body tissue, and means for contracting the loop, thereby to sever the encircled tissue from the remainder of the body, tissue retrieving means comprising:

tissue-engaging means, manipulating means connected to said engaging means, instrument for manipulation of said engaging means to engage tissue encircled by said loop, for removal of the tissue on the engaging means following severance of the tissue, and means for manually effecting rotational adjustment of the position of said engaging means relative to said loop, about a an axis extending longitudinally of the open-snare instrument for engagement of said engaging means which a selected portion of encircled tissue extending from either side of said loop.

10. A combination as defined in claim 9 wherein said instrument is a nasal snare instrument, said snare loop is adapted for reception in a nostril, and said engaging means is adapted for reception in a nostril together with said snare loop.

11. A combination as defined in claim 9 wherein said engaging means comprises a barb movable between a contracted position assumed during insertion into encircled tissue to engage the same, and an expanded position assumed upon said removal of the tissue on the engaging means.

12. In combination with a surgical open-nasal snare instrument having a longitudinally extending barrel, a snare loop projecting longitudinally outwardly from a distal end of the barrel and adapted for reception in a nostril for encircling projecting body tissue, and means carried by the barrel for contracting the loop, thereby to sever the encircled tissue from the remainder of the body, tissue-retrieving means comprising:

a manipulating rod having a longitudinal axis extending between distal and proximal ends thereof, tissue-engaging means connected to said rod adjacent to the distal end thereof and adapted for reception in a nostril together with said snare loop, a carrier supporting said rod for longitudinal movement of the rod thereon, in the direction of its distal end, and means for mounting said carrier on said barrel rotatably therearound about the longitudinal axis thereof, for manually adjusting the position of said engaging means relative to said loop, said engaging means being manipulated by said rod movement to engage a selected portion of tissue encircled by said loop and extending from either side of the loop, for removal of the tissue on the engaging means following severance of the tissue.

13. A combination as defined in claim 12 further including means for interengaging said rod and said carrier to releasably maintain said engaging means in a tissueengaging longitudinal disposition.

14. A combination as defined in claim 12 wherein said tissue-engaging means comprises a barb connected to said rod adjacent to the distal end thereof for pivotal movement about a transverse axis between contracted and expanded positions of the barb, wherein the barb extends from said transverse axis towards the proximal end of the rod at respective lesser and greater angles to said longitudinal axis thereof, and further including stop means interposed between said barb and said rod for limiting said pivotal movement to movement between said positions.

15. A combination as defined in claim 12 wherein said means for expanding and contracting said snare loop includes a finger grip, and further including a finger-engageable handle on said rod adjacent to the proximal end of the rod, said handle being disposed in the vicinity of said finger grip, for manual control of the movement of both said snare loop and said rod by the same hand.

* * * * *

UNITED STATES PATENT AND TRADEMARK OFFICE
CERTIFICATE OF CORRECTION

PATENT NO. : 4,619,260
DATED : October 28, 1986
INVENTOR(S) : John W. Magill and Carl F. Wurster It is certified that error appears in the above-identified patent and that said Letters Patent are hereby corrected as shown below:

Column 1, line 13, correct "lopped" to read -- looped --.

Column 5, line 23, correct "barrle" to read -- barrel --.

Column 9, line 20, after "only" insert -- by --.

Column 11, line 15, after "means," start a new sub-paragraph with the insertion of the words -- means for mounting said manipulating means on said -- before "instrument".

Column 11, line 21, cancel "a".

Signed and Sealed this

Twenty-fourth Day of March, 1987

Attest:

DONALD J. QUIGG

Attesting Officer

Commissioner of Patents and Trademarks